(12) United States Patent
Tuma

(10) Patent No.: US 11,305,291 B2
(45) Date of Patent: Apr. 19, 2022

(54) RACK FOR A FILTRATION DEVICE

(71) Applicant: Siemens Healthcare Diagnostics Inc., Tarrytown, NY (US)

(72) Inventor: Claus Tuma, Lauf an der Pegnitz (DE)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 742 days.

(21) Appl. No.: 16/495,244

(22) PCT Filed: Feb. 18, 2017

(86) PCT No.: PCT/US2017/018541
§ 371 (c)(1),
(2) Date: Sep. 18, 2019

(87) PCT Pub. No.: WO2017/143310
PCT Pub. Date: Aug. 24, 2017

(65) Prior Publication Data
US 2021/0146370 A1 May 20, 2021

Related U.S. Application Data

(60) Provisional application No. 62/296,723, filed on Feb. 18, 2016.

(51) Int. Cl.
*B01L 9/00* (2006.01)
*G01N 1/40* (2006.01)
(Continued)

(52) U.S. Cl.
CPC .............. *B01L 9/54* (2013.01); *G01N 1/4077* (2013.01); *G01N 35/0099* (2013.01);
(Continued)

(58) Field of Classification Search
CPC ........ B01L 9/54; B01L 3/00; B01L 2200/025; B01L 2200/026; B01L 2200/04;
(Continued)

(56) References Cited

U.S. PATENT DOCUMENTS

| 4,604,363 A | 8/1986 | Newhouse et al. |
| 5,231,029 A | 7/1993 | Wootton et al. |
| (Continued) | | |

FOREIGN PATENT DOCUMENTS

GB      1427034      3/1976

OTHER PUBLICATIONS

International Search Report dated May 18, 2017 in corresponding PCT Application No. PCT/US2017/018541.

*Primary Examiner* — Benjamin R Whatley
*Assistant Examiner* — Curtis A Thompson

(57) ABSTRACT

A rack for a diagnostic robot with at least one support for at least one container; at least one gas-outlet to supply the at least one container with a gas at a predefined but individually adjustable pressure level; a first gas pump to generate a gas at a predefined super-atmospheric pressure level; a second gas pump to generate a gas at a pre-defined sub-atmospheric pressure level; a first tubing system attached to the first gas pump and holding the gas generated by the first gas pump; a second tubing system attached to the second gas pump and holding the gas generated by the second gas pump; and at least one tube bridge, wherein one end of the bridge connects via a first valve into the first tubing system and the other end of the bridge connects via a second valve into the second tubing system, and wherein the at least one gas-outlet is connected to the center of the bridge.

20 Claims, 3 Drawing Sheets

(51) Int. Cl.
*G01N 35/00* (2006.01)
*G01N 35/02* (2006.01)
G01N 35/04 (2006.01)
B01D 29/085 (2006.01)
B01D 35/02 (2006.01)
A61M 1/00 (2006.01)
B01D 61/22 (2006.01)
B01D 61/00 (2006.01)
G01N 1/30 (2006.01)
B01L 3/00 (2006.01)

(52) U.S. Cl.
CPC ............ *G01N 35/026* (2013.01); *A61M 1/00* (2013.01); *B01D 29/085* (2013.01); *B01D 35/02* (2013.01); *B01D 61/00* (2013.01); *B01D 61/22* (2013.01); *B01L 3/00* (2013.01); *B01L 2200/025* (2013.01); *B01L 2200/026* (2013.01); *B01L 2200/04* (2013.01); *G01N 1/30* (2013.01); *G01N 2001/4088* (2013.01); *G01N 2035/00475* (2013.01); *G01N 2035/0412* (2013.01)

(58) Field of Classification Search
CPC ............ G01N 1/4077; G01N 35/0099; G01N 35/026; G01N 1/30; G01N 2001/4088; G01N 2035/00475; G01N 2035/0412; G01N 2035/00287; G01N 2035/0403; G01N 1/31; A61M 1/00; B01D 29/085; B01D 35/02; B01D 61/00; B01D 61/22
See application file for complete search history.

(56) References Cited

U.S. PATENT DOCUMENTS

| | | | |
|---|---|---|---|
| 5,484,572 A * | 1/1996 | Katakura | A61B 10/0045 422/534 |
| 2002/0011276 A1* | 1/2002 | Sander | F04B 43/043 141/59 |
| 2003/0080045 A1* | 5/2003 | Zuk, Jr. | B01D 29/05 210/416.1 |
| 2003/0157721 A1* | 8/2003 | Turner | B01L 3/50853 436/148 |
| 2004/0195758 A1* | 10/2004 | Cost | G07D 11/13 271/177 |
| 2006/0175291 A1 | 8/2006 | Hunt et al. | |
| 2008/0290040 A1 | 11/2008 | Kane et al. | |
| 2010/0276309 A1* | 11/2010 | Murasato | B01L 3/502715 206/219 |
| 2010/0320134 A1 | 12/2010 | Zuk, Jr. | |
| 2012/0315664 A1* | 12/2012 | Friedrich | G01N 1/4077 435/34 |
| 2014/0110349 A1 | 4/2014 | Bangert et al. | |
| 2015/0153257 A1* | 6/2015 | Olivier | B01D 63/087 422/534 |

* cited by examiner

RACK FOR A FILTRATION DEVICE

CROSS-REFERENCE TO RELATED APPLICATIONS

This application claims priority of U.S. Provisional Application No. 62/296,723, filed Feb. 18, 2016.

FIELD

The present invention generally relates to a rack which provides utilities to a filtration device, wherein the filtration device comprises at least a container, a carrier, a filter membrane and a supporting body. The utilities comprise a gas, e.g. air at adjustable pressure. The filtration device preferably is the one described in US 2012/0315664, the disclosure of which is incorporated herein by reference in its entirety.

BACKGROUND

Microscopy is a widely used method in analysis. In particular in the field of "life sciences", it is an indispensable tool in order, for example, to characterize tissue and cells. Object carriers have become the established "interface" between the medium to be examined and the imaging components of a microscope. These are glass plates measuring 26×76 mm (ISO 8255-2) with a thickness of from 1 to 1.5 mm. The objects are, for example, applied to the object carrier in a thin layer and can be covered with a cover glass, which, as a rule, measures 18×18 mm and is 0.16 mm thick. Objects are, for example, sections of tissue surrounded by a film of liquid.

Filtration is also a widely used technique, in particular for separating solids of different sizes from each other and/or from liquids. When microscopy and filtration are combined, following the filtration process, the filtration residue can be examined microscopically.

To enable this process to be used routinely and inexpensively for medical diagnosis, for example during the examination of tumor cells filtered from a blood sample (see e.g. US-A-2012/021435 or US-A-2014/0110349), it is necessary to provide a simple and inexpensive solution, which can also be carried out by untrained personnel. Minimization of manual process steps also results in an improved potential for standardization and the avoidance of any impairment of the quality of the results.

US-A-2012/0315664 describes an improved assembly and method for the filtration of liquids. The assembly comprises a carrier, a filter membrane and a supporting body. The supporting body is arranged and/or formed in a recess of the carrier. The filter membrane is arranged evenly and/or flat on the supporting body.

The carrier typically is an object carrier, in particular for microscopy, which is made of glass or plastic, in particular polycarbonate. The supporting body can be textured, in particular porous. The texture determines the number of support points for the filter membrane and enables filtered liquid to drain off after passing through the filter membrane. The supporting body, likewise, can be made of plastic, in particular polycarbonate, or of a ceramic. The use of an object carrier as a carrier for the filter membrane facilitates simple handling and use in standard devices.

For filtration the object carrier is placed over a lid of a container so that the filter membrane/supporting body matches with a corresponding opening in the lid such that the gap between the object carrier and the opening in the lid is air sealed. The container is connected to tubes supplying the container with a gas at operator controlled super- and sub-atmospheric pressure, thereby allowing control of the filtration process as described e.g. in US-A-2014/0110349.

Typically, the container is a replaceable part of a rack. The rack can be placed in a diagnostic robot, e.g. a pipette robot which performs automated procedures such as pipetting one or more liquids from one or more reservoirs onto the object carrier which is reversibly fixed on the container lid. The object carrier and/or the container may then be transferred to an analyzing station inside or outside the robot.

So far, when placing the container including the object carrier in the rack the container has to be manually attached to the pressure/vacuum tubes provided by the robot. Typical robots provide the pressure and the vacuum at different but constant pressure levels—one level for the super and one level for the sub atmospheric pressure. If the container has to be maintained at a desired pressure level which is different from the level(s) provided by the robot the desired pressure level has to be generated by opening and closing valves to both tubes the super and the sub atmospheric tube at to be determined individual frequencies.

Thus, it is apparent that the above described procedure still requires a high degree of manual labor and skills, besides that a permanent on/off cycling of valves does not contribute to an extended life time of the valves/diagnose robot.

It was, therefore an object of the present invention to provide for an improved rack for a pipette robot which rack provides utilities, i.e. at least a gas, preferably air at pre-defined but adjustable pressure levels to a container of a filtration assembly comprising the container, a carrier, a filter membrane and a supporting body. Moreover, the rack should be designed to be used routinely and inexpensively for medical diagnosis, for example for the examination of tumor cells filtered from a blood sample. Accordingly, it was an object to develop a simple and inexpensive device, which can also be operated by untrained personnel without jeopardizing the quality of the diagnostic results.

SUMMARY

This object is achieved with a rack fora diagnose robot comprising:
- at least one support for at least one container to firmly hold the container in a pre-determined position of the rack;
- at least one gas-outlet to supply the at least one container with a gas at a pre-defined but individually adjustable pressure level
- a first gas pump to generate a gas at a pre-defined super-atmospheric pressure level
- a second gas pump to generate a gas at a pre-defined sub-atmospheric pressure level
- a first tubing system attached to the first gas pump and holding the gas generated by the first gas pump
- a second tubing system attached to the second gas pump and holding the gas generated by the second gas pump
- at least one tube bridge, wherein one end of the bridge connects via a first valve into the first tubing system and the other end of the bridge connects via a second valve into the second tubing system, and wherein the at least one gas-outlet is connected to the center of the bridge.

Advantageous embodiments of the device according to the invention and its use may be derived from the respective dependent claims. The features of the main claim can be combined with the features of one or more dependent claims and the features of the dependent claims can be combined with features from other dependent claims.

BRIEF DESCRIPTION OF THE DRAWINGS

Preferred embodiments of the invention with advantageous developments according to the features of the dependent claims are explained in more detail below with reference to the figures, but without being restricted thereto.

The figures show.

DETAILED DESCRIPTION OF THE INVENTION

Figure 1:
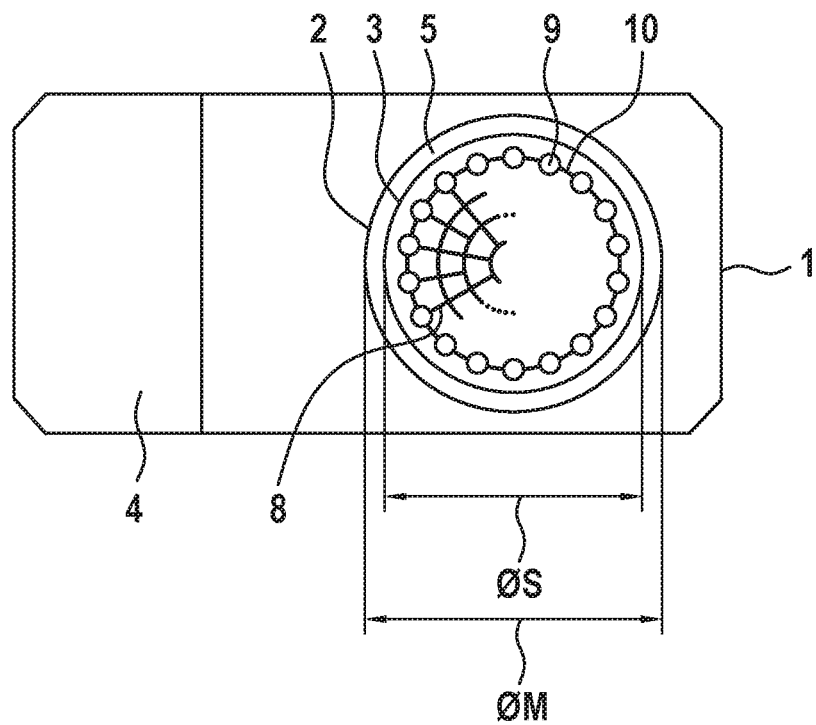
FIG. 1 a schematic representation of an object carrier including the filtration assembly in top view with a carrier, a supporting body and a filter membrane (not part of the present invention)

A "rack" is a standardized insert device for diagnostic robots which meets the size limitations set by the diagnostic robot, preferably by diagnostic robots from different manufacturers so that it can be used independently from the manufacturer of the given diagnostic robot. It fits the guide rail system of the inside of the robot (if present) so that it can be transferred to different pre-selected diagnostic stations within the robot. If necessary, the rack can be connected or is automatically connected upon insertion into the robot to utilities provided by the robot, such as electric power, digital and/or analog data input/output, fluids, gases etc. Racks can be provided for example for analytic test tubes, well plates or even hold complete diagnostic analytical devices.

The Filtration System

The object carrier including the filtration assembly is described in detail in US-A-2012/0315664, and comprises a carrier, a filter membrane and a supporting body. The supporting body is arranged and/or formed in a recess of the carrier. The filter membrane is arranged evenly and/or flat on the supporting body.

During filtering, the supporting body provides mechanical support for the filter membrane, thus enabling large quantities of liquid to be filtered in a reasonable time. Filter membranes, which can only be embodied as very thin, are, for example, filter membranes produced by particle bombardment from films with precisely defined through-pores or holes. Good support with the aid of the supporting body in the form of numerous, uniformly distributed support points is essential for the use of filter membranes of this kind as filters.

The carrier can have a thickness in the region of 1 to 1.5 mm, a length in the region of 75 to 76 mm and a width in the region of 25 to 26 mm. The filter membrane can have a thickness in the region of 1 to 20 µm, preferably in the region of 10 µm, and a diameter in the region of 25 mm. These dimensions make the carriers suitable for use in the most commonly used holdings in standard devices for object carriers.

The recess in the carrier can have the same size as the supporting body. This facilitates good holding of the supporting body in the carrier. On the other hand the supporting body can be produced integrally from the carrier material. In the second case, a permanently stable assembly is achieved. The supporting body can have a circular design and the filter membrane can also have a circular design. This facilitates use in systems with circular feed pipes and circular discharge pipes for fluids. A round embodiment also facilitates microscopy, because the entire circular region can be optically resolved in the microscope's field of view.

The supporting body can comprise channels formed on a side facing the filter membrane, which are in fluidic contact with the filter membrane. These channels facilitate good drainage of the filtered liquid from the filter membrane and hence good passage of liquid to be filtered through the filter membrane.

The filter membrane can be a track etched filter membrane made of polycarbonate film and comprises holes with a diameter of micrometers, in particular 8 µm and a hole density of 1% to 80% (as the ratio of the perforated area to the overall area), in particular a hole density of 105 holes per square centimeter.

The assembly shown in FIG. 1 comprises a carrier (1) and a supporting body (3) arranged in a recess of the carrier (1). The carrier (1) is embodied as even in the form of an object carrier for light microscopy. In a region disposed at a distance from supporting body (3), an area can be embodied as a grip (4) in that the surface is roughened, for example, in this region.

Figure 2:
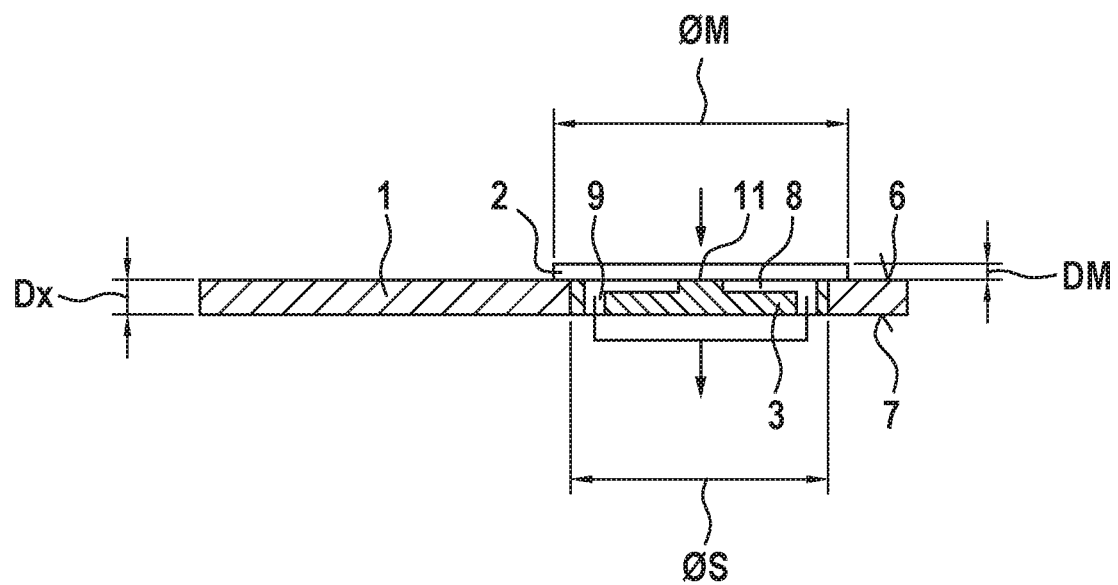
FIG. 2 a schematic sectional view through the assembly shown in FIG. 1 (not part of the present invention)

As FIGS. 1 and 2 show, a circular, film-type filter membrane (2) is arranged evenly on a front side (6) of the carrier (1) and the supporting body (3). The circular filter membrane (2) has, for example, a circular diameter OM in the region of 25 mm and a thickness DM in the region of 10 µm. In the edge region (5), the filter membrane (2) is mechanically connected to the carrier, for example by welding or adhesion. The circular supporting body (3) is arranged below the filter membrane (2). The supporting body has, for example, a circular diameter ØS in the region of 23 mm and a thickness Dx corresponding to the thickness of the carrier. The filter membrane (2) lies evenly on the supporting body (3), wherein deviations from a planar contact surface between the supporting body (3) and filter membrane (2) can be, for example, maximum 100 µm. The supporting body (3) and the carrier (1) can be formed as one integral piece or the circular supporting body (3) can be arranged in a circular recess passing right through the thickness Dx of the carrier, in particular connected in a mechanically stable way to the carrier (1). In addition to circular shapes of the supporting body (3) and the recess, other shapes, for example rectangular or triangular shapes, are possible. A positive contact between the supporting body (3) and the recess of the carrier (1) is of advantage here.

As shown in FIGS. 1 and 2, channels (8) are formed in the surface of the supporting body (3) on a front side (6). In order to keep the channel density of the channels (8) on the surface in the direction of edge region (5) substantially constant, the number of channels (8) increases in the direction of the edge (5) going from the mid-point (11).

Drainage holes (9) passing completely through the thickness Dx of the carrier (1) or supporting body (3) are arranged close to the edge region (5) of the filter membrane (2) in the supporting body (3) or in the carrier (1) or in the contact region between the supporting body (3) and carrier (1). The channels (8) end in the drainage holes (9). Fluid flowing through the filter membrane (2) can come through the channels (8) and the drainage holes (9) from the front side (6) of the carrier (1) and arrive at the rear side (7) of the carrier (1) and be transported away from there. Good uniform passage through filter membrane (2) and good filtering of the fluid are facilitated. In particular, a uniform pressure drop over the entire filter membrane surface is achieved.

Alternatively, if ceramic is used as the material for the supporting body (3), a porous layer can be formed on the surface of the supporting body (3), which, similarly to channels (8) or (10), permits uniform drainage of a fluid. If the supporting body (3) is completely made of a porous material, the drainage holes (9) and channels (8) or (10) can be provided by the porosity.

The Container

The container's main object is to receive the filtrate leaving the rear side (7) of the carrier (1) and to provide a stable support for the filtration assembly holding it in a fixed, predetermined position so that it can reliably be accessed by the various tools of the robot. It can in principal have any cross sectional shape, like round, oval, square, rectangular, hexagonal or even polygonal, however it seems that a round cross sectional shape (i.e. cylindrical or cone shaped) is the most economic and useful shape, which is, therefore, preferred. Likewise it can be made of nearly any material, the only restriction would be for material which could interfere with the filtrate if the filtrate is of analytical interest or is so reactive that it could destroy the container wall and, thus, contaminate the robot. Most common materials used are polyethylene, polypropylene, polyamide, polycarbonate, polystyrene and the like or glass or ceramic or metal, like stainless steel.

Figure 3:
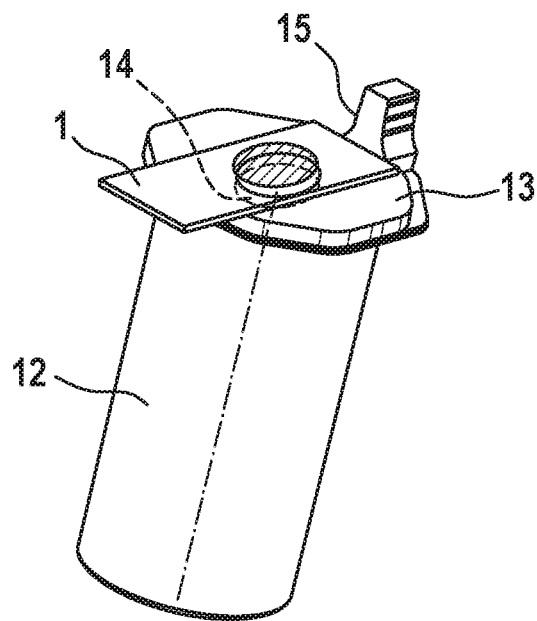
FIG. 3 a perspective view of a container

FIG. 3 shows a container (12) with closed lid (13) and object carrier (1) in place. In order to provide a stable support for the filtration assembly and in order to hold it in a fixed, predetermined position the container (12) should be designed to lock into a predetermined position once placed in the rack. This can be achieved for example with a protrusion/notch system (not shown) where e.g. the protrusion is located at the rack-site and the notch on the container wall (or vice versa), so that the container only slides into its correct position when the protrusion matches the notch. Other systems that can be implemented for this purpose are a bayonet lock system or a guide rail system e.g. with vertical or spiral grooves (not shown).

The container (12) is equipped with a lid (13) that covers the container (12). The lid (13) is preferably provided with a seal against and around the rim of the container top (not shown). The lid (13) may be removable but is preferably fixed to the rim, e.g. welded to the rim. The lid (13) is also provided with an opening (14) that matches the size and form of the filter membrane/supporting body (2, 3) of the object carrier (1) which is placed over the opening (14) in the lid (13) of the container (12) for filtration of a sample. The gap between the object carrier and the opening (14) in the lid (13) preferably is air sealed which can be established with an appropriate flexible ring (not shown) which is fixed on the rim of the lid opening (14) or which is an integral part of the lid (13).

Either the lid (13) or the container (12), preferably the container (12) is equipped with an adapter (15) which matches the outlet (16) on the rack for a gas, preferably air, at a pre-defined, adjustable pressure level. The adapter (15)/outlet (16) pair can e.g. be designed as needle/diaphragm, CPC coupling, bayonet coupling or the like (not shown). The location of the adapter (15)/outlet (16) pair is not critical but should preferably be in an area where the risk of contamination with filter products is minimal, e.g. on the upper part of the container side wall (with the matching outlet (16) on the rack being positioned so as to match with the adapter (15) on the container (12)).

The Rack

Figure 4:
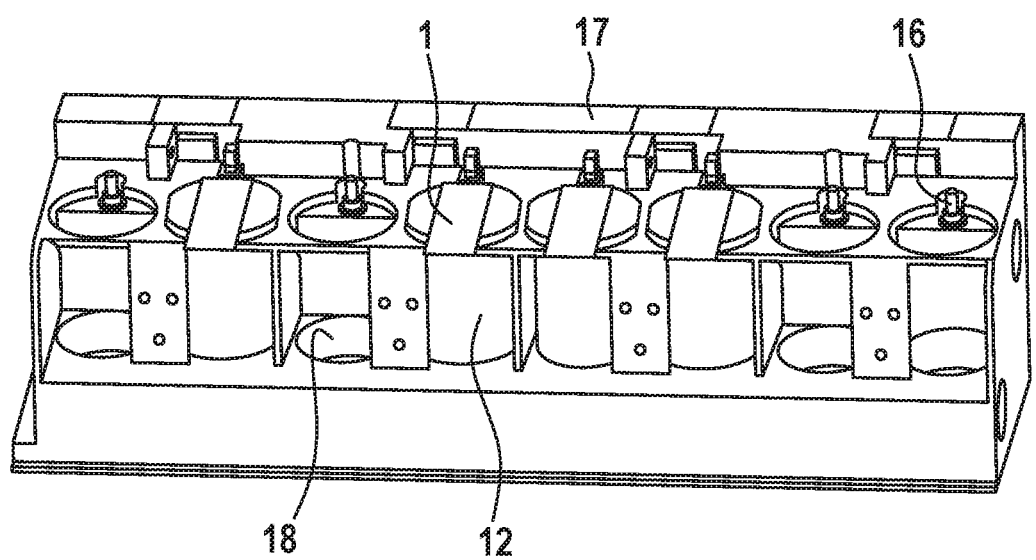
FIG. 4 a 3D picture of an embodiment of the rack with 4 containers inserted

The rack according to the present invention—an embodiment of which is shown in FIG. 4—provides support for one or more, preferably up to eight containers (12) e.g. for performing lysis and filtration of whole blood samples. The containers (12) hold the filtrates and the lids (13) are designed to hold an object carrier (1) each, wherein the object carrier (1) includes a filtration assembly (2, 3).

The rack (17) according to the invention provides an outlet (16) for each container for a gas, preferably air, at a pre-defined, adjustable pressure level. The form of the gas-outlet matches with a corresponding adapter (15) on the container (12) or lid (13) so that a gas-leak-proof connection is established between the container (12) or lid (13) and the rack (17) preferably upon insertion of the lid covered container (12, 13) into the container-support (18) of the rack (17).

Figure 5:
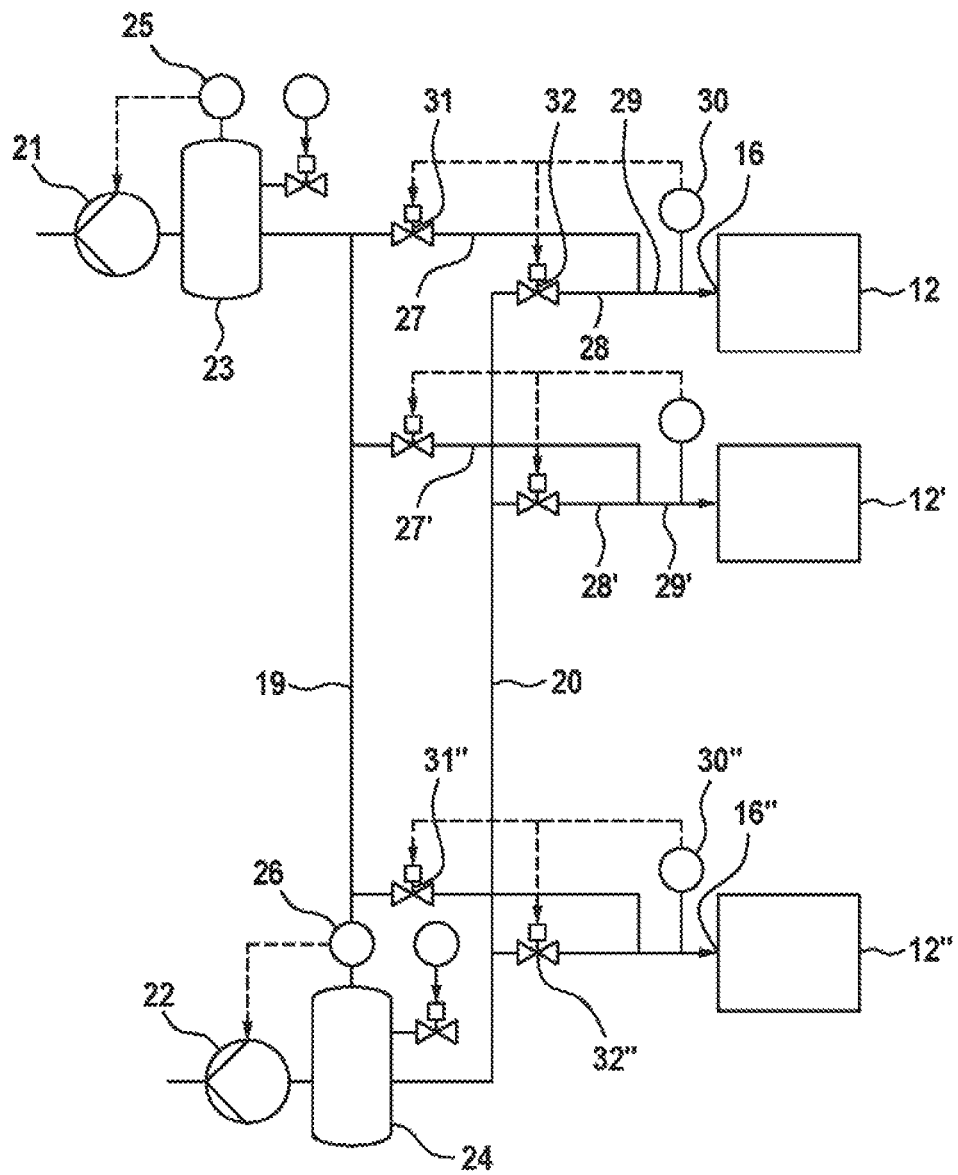
FIG. 5 a schematic view of the rack showing the tubing and arrangement of valves, pumps etc.

As shown in FIG. 5 the rack (17) further includes two tubing system for a gas, preferably air, at different pressure levels. A first tubing system (19) for a gas, preferably air, at a pre-defined super-atmospheric pressure, and a second tubing system (20) for a gas, preferably air, at a pre-defined sub-atmospheric pressure. The rack (17) further includes two gas, preferably air, pumps (21, 22), a first one (21) to generate a pre-defined super-atmospheric pressure, and a second one (22) to generate a pre-defined sub-atmospheric pressure (vacuum). Optionally, gas storage tanks (23, 24) can be included to buffer pressure differences when valves are opened and containers (12, 12', 12") are filled/evacuated, and to provide for sufficient gas volume. Preferably, the pumps (21, 22) are computer controlled using the gas pressure information from the storage tanks' pressure gauges (25, 26).

Each container (12, 12', 12") is attached via the gas pressure outlet (16) on the rack (17) to a gas tube-bridge, the two ends (27, 28 or 27', 28') of which are connected to the gas tubing system, the first end (27, 27') attaching to the super-atmospheric tubing system (19) and the second end (28, 28') attaching to the sub-atmospheric tubing system (20). The center part (29, 29') of the gas bridge is attached to the gas pressure outlet (16, 16") on the rack (17) leading to the container (12, 12"). Each center part (29, 29') of each tube-bridge preferably comprises a pressure gauge (30, 30") providing digital or analog gas pressure information to a corresponding data-signal-outlet on the rack (17) (not shown) to allow for adjusting the gas pressure, preferably for computer controlled gas pressure adjustment. At or near the two points where the gas bridge leads into the super-atmospheric tubing system (19) and the sub-atmospheric tubing system (20) respectively, gas valves (31, 32) are positioned which actively control the access of each container to either the super-atmospheric tubing system (19) via the first gas valve (31, 31") or the sub-atmospheric tubing system (20) via the second gas valve (32, 32"). Thus, the pressure level in each container can be individually adjusted to the pre-defined level by opening the first or second valve for a time period sufficient to reach the pre-defined pressure level. The pressure level in each container can be monitored with optional pressure gauge (30, 30"). For the computer controlled pressure adjustment the data from pressure gauge (30, 30") are used to activate the gas valves (31, 31") and (32, 32").

The rack (17) preferably also comprises means for holding the container(s) and the filtration assembly in position (not shown). This can for example be accomplished with conventional straps or clamps using attachments like elastic velcro or latches with a draw bail.

The rack (17) can be made of plastic material, e.g. polypropylene, polyamide or polycarbonate; preferably the rack (17) is made using 3D-printing technology.

Use

With the above-described rack including the described filtration assembly whole blood samples can be filtered. This separation predominantly isolates circulating rare cells with some white blood cells and no red blood cells. After isolating the cells, the cells are fixed and washed. The process can be stopped (by applying super-atmospheric pressure to the container) e.g. for bio banking slides with rare cells or can be continued with automated procedures for e.g.: molecular detection of proteins by immunocytochemistry (ICC); RNA in-situ hybridization (ISH); or cytological morphology by chromogenic dye staining (H&E). Alternatively the carriers can be used to extract cellular material for other detection methods which are not automated in the given procedure, such as PCR or FISH analysis for DNA or automated immunoassays.

The method allows cells to be fixed with formaldehyde and permeabilized with detergent to help expose intracellular antigens. The method also allows series of wash steps to wash away unbound antibody and probe, blocking steps to reduce non-specific binding and incubation steps for multiple step assays. The methods further allows using DAPI (4′,6-diamidino-2-phenylindole), a fluorescent DNA stain to stain the nuclei of the cells and the application of cover media to help preserve the fluorescent intensity of the probes.

Illustration of Use

A rack (17) like the one shown in FIG. 4 (without containers) is mounted in a diagnostic robot (e.g. Hamilton Starlet). All container supports (18) are empty. All valves are in position "open". The gas used is air. A test run is then performed in which all functions of the rack (valves, pumps etc.) are checked for proper operation. Next the local atmospheric pressure is determined and set as a reference pressure for the subsequent procedures. It is verified that all internal cavities are at reference pressure level (local atmospheric pressure).

An object carrier (1) which includes a filtration assembly (2, 3) is placed over the opening (14) of a lid-covered container (12, 13). This object carrier/container assembly is then inserted into one of the container supports in the rack (17) and attached via adapter (15) to the gas-outlet (16) on the rack (17), thereby establishing a gas leak proof connection between the container and the rack.

A sample, e.g. a whole blood sample is then applied onto the filtration assembly (2, 3).

An operator or a computer program then determines the subsequent operations of the filtration procedure. Super- and sub-atmospheric pressure levels can be applied to the filtration assembly (2, 3) for individually pre-selected periods of time. The applied pressure levels—which are normalized to the reference pressure level (local atmospheric pressure)—of course depend on the maximum mechanical stress level allowed for the sample to be filtered and other factors known to the skilled person, but typically range from 1 to 100 hPa, preferably 3 to 50 hPa, more preferably 4 to 30 hPa and most preferably from 5 to 10 hPa above the reference pressure level for the super-atmospheric pressure; and from 5 to 200 hPa, preferably 10 to 100 hPa, more preferably 15 to 75 hPa and most preferably from 20-50 hPa below the reference pressure level for the sub-atmospheric pressure.

The time range for which the sample is subjected to the sub- or super-atmospheric pressure of course also depends on the sample to be filtered and other factors known to the skilled person and can vary from a fraction of a second to hour ranges but are typically within several seconds up to a few minutes.

The sub-/super-atmospheric pressure cycle can be repeated as many times as necessary for a given sample.

Each container in the rack (17) can be addressed individually and independently with pre-determined sub-/super-atmospheric pressure cycles.

EXAMPLE

For example embodiments being herein described, it will be obvious that the same may be varied in many ways. Such variations are not to be regarded as departing from the spirit and scope of the present invention, and all such modifications, as would be obvious to one skilled in the art, are intended to be included within the scope of the below claims.

The following example illustrates the use of the rack according to the present invention in whole blood filtration.

A rack (17) like the one shown in FIG. 4 (without containers) is mounted in a Hamilton Starlet diagnostic robot. It is equipped with one container (12), covered with a lid (13). The lid (13) has an opening (14) and holds an object carrier (1) which includes a filtration assembly (2, 3) comprising a filtration membrane and a supporting body. Via adapter (15) the container is attached to the gas-outlet (16) on the rack (17) so that a gas leak proof connection is established between the container and the rack upon insertion of the container. A device check is performed to verify proper operation of all functions of the rack (17) and to determine and set the reference pressure (local atmospheric pressure).

A whole blood sample is applied onto the filtration assembly (2, 3). The second valve (32) is then opened until pressure gauge (30) shows an air-pressure of 20 hPa (sub-atmospheric pressure relative to the reference pressure) in the container resulting in filtration of the blood.

After 30 seconds of filtration the first valve (31) is opened until pressure gauge (30) shows an air pressure of 5 hPa (super-atmospheric pressure relative to the reference pressure) in the container in order to discontinue the filtration process.

Subsequently water as a wash liquid is applied onto the filtration assembly and the filtration is started again by opening the second valve until an air pressure of 20 hPa (sub-atmospheric pressure relative to the reference pressure) is obtained.

This cycle was repeated three times before the carrier was transferred to the next station inside the robot for further analysis.

LIST OF REFERENCE NUMBERS (1) carrier
(2) filter membrane
(3) supporting body
(4) grip (of carrier)
(5) edge region (of filtration assembly)
(6) front side (of carrier)
(7) rear side (of carrier)
(8) channels (of filtration assembly)
(9) drainage holes (of filtration assembly)
(10) channels (of filtration assembly)
(11) mid point (of filtration assembly)
(12) container
(13) lid

(14) lid opening
(15) adapter (on container)
(16) pressure outlet (on rack)
(17) rack
(18) container support (on rack)
(19) super-atmospheric tubing system (inside rack)
(20) sub-atmospheric tubing system (inside rack)
(21) super-atmospheric pressure gas pump (inside rack)
(22) sub-atmospheric pressure gas pump (inside rack)
(23) super-atmospheric pressure gas tank (inside rack)
(24) sub-atmospheric pressure gas tank (inside rack)
(25) super-atmospheric storage tanks' pressure gauge (inside rack)
(26) sub-atmospheric storage tanks' pressure gauges (inside rack)
(27) super-atmospheric end of gas-bridge (inside rack)
(28) sub-atmospheric end of gas-bridge (inside rack)
(29) center part of gas bridge (inside rack)
(30) pressure gauge in gas bridge (inside rack)
(31) first gas valve to super-atmospheric tubing system (inside rack)
(32) second gas valve to sub-atmospheric tubing system (inside rack)

Inventive Subject Matter (ISM)

The following is a list of the inventive subject matter (ISM):
1. A rack for a diagnose robot comprising:
   at least one support for at least one container to firmly hold the container in a pre-determined position of the rack;
   at least one gas-outlet to supply the at least one container with a gas at a pre-defined but individually adjustable pressure level
   a first gas pump to generate a gas at a pre-defined super-atmospheric pressure level
   a second gas pump to generate a gas at a pre-defined sub-atmospheric pressure level
   a first tubing system attached to the first gas pump and holding the gas generated by the first gas pump
   a second tubing system attached to the second gas pump and holding the gas generated by the second gas pump
   at least one tube bridge, wherein one end of the bridge connects via a first valve into the first tubing system and the other end of the bridge connects via a second valve into the second tubing system, and wherein the at least one gas-outlet is connected to the center of the bridge.
2. Rack according to ISM 1, wherein the gas is air.
3. Rack according to ISM 1 or 2, further comprising a pressure gauge in the center part of the at least one tube bridge.
4. Rack according to one of ISM 1-3, further comprising a first gas storage tank arranged between the first gas pump and the first tubing system, and a second gas storage tank (24) arranged between the second gas pump and the second tubing system.
5. Rack according to one of ISM 1-4, further comprising input and/or output ports for power supply and/or digital and/or analog data.
6. Rack according to one of ISM 1-5, wherein the at least one container is held in position with straps or clamps.
7. Rack according to one of ISM 1-6, made of plastic material.
8. Rack according to ISM 7, wherein the plastic material is polypropylene, polyamide or polycarbonate.
9. Rack according to ISM 7, made using 3D-printing technology.
10. A filtration device comprising the rack according to ISM 1 and at least one container, covered with a lid which lid exhibits an opening, wherein the lid holds an object carrier which includes a filtration assembly comprising a filtration membrane and a supporting body,
    wherein
    an adapter on the container or lid is attached to the gas-outlet on the rack so that a gas leak proof connection is established between the container or lid and the rack.
11. Method of filtering a liquid, comprising providing a filtration device according to ISM 10, followed by
    a) applying a liquid to be filtered onto the filtration assembly, opening the second valve until a pre-determined sub-atmospheric gas pressure has been generated in the container resulting in filtration of the liquid, and then optionally
    b) opening the first valve until a pre-determined super-atmospheric gas pressure has been generated in the container in order to discontinue the filtration process and then optionally
    c) applying a liquid reagent onto the filtration assembly and then optionally
    d) opening the second valve until a pre-determined sub-atmospheric gas pressure has been generated in the container resulting in filtration of the liquid
    and then optionally repeating one or more of steps b)-d).
12. Use of a rack according to one of the ISM 1-9 for whole blood filtration.
13. Use of a rack according to one of the ISM 1-9 for the isolation of circulating rare cells.
14. Use of a rack according to one of the ISM 1-9 for bio banking carriers with rare cells.
15. Use of a rack according to one of the ISM 1-9 for molecular detection of proteins by immunocytochemistry (ICC); or for RNA in-situ hybridization (ISH); or for cytological morphology by chromogenic dye staining (H&E); or for PCR or FISH analysis; or for DNA immunoassays; or for automated immunoassays; or for DAPI (4',6-diamidino-2-phenylindole) staining of cell nuclei; or for the application of cover media to help preserve the fluorescent intensity of probes.

The invention claimed is:
1. A filtration device, comprising:
    at least one container;
    a rack for a diagnostic robot, the rack comprising:
        at least one support for the at least one container to firmly hold the at least one container in a pre-determined position of the rack;
        at least one gas-outlet to supply the at least one container with a gas at a pre-defined but individually adjustable pressure level;
        a first gas pump to generate a pre-defined super-atmospheric pressure level of the gas;
        a second gas pump to generate a pre-defined sub-atmospheric pressure level of the gas;
        a first tubing system attached to the first gas pump and holding the gas generated by the first gas pump;
        a second tubing system attached to the second gas pump and holding the gas generated by the second gas pump;
        at least one tube bridge, wherein one end of the bridge connects via a first valve into the first tubing system and the other end of the bridge connects via a second valve into the second tubing system, and wherein the at least one gas-outlet is connected to the center of the bridge;

a lid covering the at least one container, wherein the lid exhibits an opening, wherein the lid holds an object carrier which includes a filtration assembly comprising a filtration membrane and a supporting body; and an adapter on the at least one container or lid, wherein the adapter is attached to the at least one gas-outlet on the rack so that a gas leak proof connection is established between the at least one container or lid and the rack.

2. The filtration device according to claim 1, wherein the gas is air.

3. The filtration device according to claim 1, wherein the rack further comprises a pressure gauge in the center part of the at least one tube bridge.

4. The filtration device according to claim 1, wherein the rack further comprises a first gas storage tank arranged between the first gas pump and the first tubing system, and a second gas storage tank arranged between the second gas pump and the second tubing system.

5. The filtration device according to claim 1, wherein the rack further comprises input and/or output ports for power supply and/or digital data and/or analog data.

6. The filtration device according to claim 1, wherein the rack further comprises straps or clamps that hold the at least one container and the filtration assembly in position.

7. The filtration device according to claim 1, wherein at least a portion of the rack is made of plastic material.

8. The filtration device according to claim 7, wherein the plastic material is at least one of polypropylene, polyamide, or polycarbonate.

9. The filtration device according to claim 1, wherein at least a portion of the rack is made using 3D-printing technology.

10. A method of filtering a liquid, the method comprising the steps of:
(a) obtaining a filtration device, comprising:
at least one container;
a rack for a diagnostic robot, the rack comprising at least one support for the at least one container to firmly hold the at least one container in a pre-determined position of the rack, at least one gas-outlet to supply the at least one container with a gas at a pre-defined but individually adjustable pressure level, a first gas pump to generate a pre-defined super-atmospheric pressure level of the gas, a second gas pump to generate a pre-defined sub-atmospheric pressure level of the gas, a first tubing system attached to the first gas pump and holding the gas generated by the first gas pump, a second tubing system attached to the second gas pump and holding the gas generated by the second gas pump, at least one tube bridge having one that connects via a first valve into the first tubing system and another end that connects via a second valve into the second tubing system, and wherein the at least one gas-outlet is connected to the center of the bridge;
a lid covering the at least one container, wherein the lid exhibits an opening, wherein the lid holds an object carrier which includes a filtration assembly comprising a filtration membrane and a supporting body; and
an adapter on the at least one container or lid, wherein the adapter is attached to the at least one gas-outlet on the rack so that a gas leak proof connection is established between the at least one container or lid and the rack;

(b) applying a liquid to be filtered onto the filtration assembly of the filtration device; and (c) opening the second valve until the pre-determined sub-atmospheric gas pressure has been generated in the at least one container, resulting in filtration of the liquid.

11. The method according to claim 10, further comprising one or more steps selected from:
(d) opening the first valve until the pre-determined super-atmospheric gas pressure has been generated in the at least one container in order to discontinue the filtration process;
(e) applying a liquid reagent onto the filtration assembly;
(f) opening the second valve until the pre-determined sub-atmospheric gas pressure has been generated in the at least one container resulting in filtration of the liquid reagent; and
(g) repeating one or more of steps (d)-(f).

12. The method according to claim 10, wherein the liquid applied in step (b) comprises whole blood.

13. The method according to claim 12, wherein the method is further defined as a method of isolating cells from whole blood.

14. The method according to claim 13, further comprising the steps of fixing and washing the isolated cells.

15. The method according to claim 14, further comprising the step of exposing the isolated cells to one or more automated assay procedures.

16. The method according to claim 10, wherein the gas is air.

17. The method according to claim 10, wherein the rack of the filtration device further comprises one or more of:
a pressure gauge in the center part of the at least one tube bridge;
a first gas storage tank arranged between the first gas pump and the first tubing system, and a second gas storage tank arranged between the second gas pump and the second tubing system;
and/or
input and/or output ports for power supply and/or digital data and/or analog data.

18. The method according to claim 10, wherein the rack further comprises straps or clamps that hold the at least one container and the filtration assembly in position.

19. The method according to claim 10, wherein at least a portion of the rack is made of plastic material.

20. The method according to claim 19, wherein the plastic material is polypropylene, polyamide or polycarbonate.

* * * * *